United States Patent
Ryan (12)

(10) Patent No.: US 6,267,761 B1
(45) Date of Patent: Jul. 31, 2001

(54) APPARATUS AND METHOD FOR SEALING AND CUTTING TISSUE

(75) Inventor: Thomas Patrick Ryan, Fort Collins, CO (US)

(73) Assignee: Sherwood Services AG, Schaffhausen (CH)

(*) Notice: Subject to any disclaimer, the term of this patent is extended or adjusted under 35 U.S.C. 154(b) by 0 days.

(21) Appl. No.: 08/925,805

(22) Filed: Sep. 9, 1997

(51) Int. Cl.[7] .................................................. A61B 18/18
(52) U.S. Cl. .............................. 606/50; 606/32; 606/41
(58) Field of Search .......................... 606/32, 41, 45–50, 606/159, 167, 185; 604/19, 22; 128/898

(56) References Cited

U.S. PATENT DOCUMENTS

| | | |
|---|---|---|
| 371,664 | 10/1887 | Brannan et al. . |
| 702,472 | 6/1902 | Pignolet . |
| 728,883 | 5/1903 | Downes . |
| 1,586,645 | 6/1926 | Bierman . |
| 2,002,594 | 5/1935 | Wappler et al. . |
| 2,011,169 | 8/1935 | Wappler . |
| 2,176,479 | 10/1939 | Willis . |
| 2,668,538 * | 2/1954 | Baker ..................................... 606/207 |
| 2,796,065 * | 6/1957 | Kapp ..................................... 606/207 |
| 3,643,663 | 2/1972 | Sutter . |
| 3,651,811 | 3/1972 | Hildebrandt et al. . |
| 3,862,630 | 1/1975 | Balamuth . |
| 3,920,021 | 11/1975 | Hiltebrandt . |
| 3,938,527 | 2/1976 | Rioux et al. . |
| 3,952,749 | 4/1976 | Fridolph et al. . |
| 4,005,714 | 2/1977 | Hiltebrandt . |
| 4,370,980 | 2/1983 | Lottick . |
| 4,552,143 | 11/1985 | Lottick . |
| 4,597,379 | 7/1986 | Kihn et al. . |
| 4,671,274 | 6/1987 | Sorochenko . |
| 4,685,459 | 8/1987 | Koch et al. . |
| 4,887,612 | 12/1989 | Esser et al. . |

(List continued on next page.)

FOREIGN PATENT DOCUMENTS

| | | |
|---|---|---|
| 0 584 787 A1 | 3/1994 | (EP) . |
| 0 853 922 A1 | 7/1998 | (EP) . |
| 401367 | 12/1973 | (SU) . |
| WO92/06642 | 4/1992 | (WO) . |

OTHER PUBLICATIONS

International Search Report—PCT/US98/18640.

International Search Report—PCT/US98/23950.

Sigel et al., "The Mechanism of Blood Vessel Closure by High Frequency Electrocoagulation", Surgery Gynecology & Obstetrics, Oct. 1965 pp. 823–831.

Bergdahl et al. "Studies on Coagulation and the Development of an Automatic Computerized Bipolar Coagulator", J. Neurosurg, vol. 75, Jul. 1991, pp. 148–151.

International Search Report PCT/US99/24869.

*Primary Examiner*—Glenn K. Dawson

(57) ABSTRACT

An axial elongate bipolar tissue sealer and method of use by a surgeon for electrosurgery on tissue has a handle. A tube may move axially relative to a chassis on the handle. The effector provides bipolar electrosurgery. A member extending from the distal end is opposite the patient end of the tube. A part on the member is transverse to the axis to conduct electrosurgery. First and second bipolar electrodes on the effector and part are electrically isolated. A generator for bipolar electrosurgery supplies the electrodes. An activator is movably supported on the handle connects to the tube and/or chassis to axially move the patient end and its effector relative to the part. Tissue and bodily fluid therebetween are sealed through application of compression and bipolar electrosurgery between the first and second electrodes. The effector and the part have complimentary sealing surfaces for partial mating engagement upon axial movement toward one another. The effector and the part can be removably attached to the distal end or member, respectively.

23 Claims, 7 Drawing Sheets

U.S. PATENT DOCUMENTS

| | | |
|---|---|---|
| 4,938,761 | 7/1990 | Ensslin . |
| 5,026,370 | 6/1991 | Lottick . |
| 5,116,332 | 5/1992 | Lottick . |
| 5,151,102 | 9/1992 | Kamiyama et al. . |
| 5,176,695 | 1/1993 | Dulebohn . |
| 5,217,458 * | 6/1993 | Parins ................................... 606/39 |
| 5,250,047 | 10/1993 | Rydell . |
| 5,258,006 | 11/1993 | Rydell et al. . |
| 5,275,615 | 1/1994 | Rose . |
| 5,277,201 | 1/1994 | Stern . |
| 5,304,203 | 4/1994 | El-Mallawany et al. . |
| 5,324,289 | 6/1994 | Eggers . |
| 5,330,471 | 7/1994 | Eggers . |
| 5,342,359 | 8/1994 | Rydell . |
| 5,342,393 | 8/1994 | Stack . |
| 5,352,222 | 10/1994 | Rydell . |
| 5,354,271 | 10/1994 | Voda . |
| 5,356,408 | 10/1994 | Rydell . |
| 5,383,897 | 1/1995 | Wholey . |
| 5,389,104 | 2/1995 | Hahnen et al. . |
| 5,391,166 | 2/1995 | Eggers . |
| 5,391,183 | 2/1995 | Janzen et al. . |
| 5,403,312 | 4/1995 | Yates et al. . |
| 5,411,520 | 5/1995 | Nash et al. . |
| 5,415,657 | 5/1995 | Taylor-Luria . |
| 5,425,739 | 6/1995 | Jessen . |
| 5,429,616 | 7/1995 | Schaffer . |
| 5,431,674 | 7/1995 | Basile et al. . |
| 5,437,292 | 8/1995 | Kipshidze . |
| 5,441,517 | 8/1995 | Kensey et al. . |
| 5,443,463 | 8/1995 | Stern et al. . |
| 5,443,464 | 8/1995 | Russell et al. . |
| 5,445,658 | 8/1995 | Durrfeld et al. . |
| 5,456,684 | 10/1995 | Schmidt et al. . |
| 5,462,546 | 10/1995 | Rydell . |
| 5,472,443 | 12/1995 | Cordis et al. . |
| 5,478,351 | 12/1995 | Meade et al. . |
| 5,484,436 | 1/1996 | Eggers et al. . |
| 5,509,922 | 4/1996 | Aranyi et al. . |
| 5,527,313 | 6/1996 | Scott et al. . |
| 5,531,744 | 7/1996 | Nardella et al. . |
| 5,540,684 | 7/1996 | Hassler, Jr. . |
| 5,558,672 | 9/1996 | Edwards et al. . |
| 5,569,241 | 10/1996 | Edwards . |
| 5,573,535 | 11/1996 | Viklund . |
| 5,585,896 | 12/1996 | Yamazaki et al. . |
| 5,626,578 | 5/1997 | Tihon . |
| 5,637,110 | 6/1997 | Pennybacker et al. . |
| 5,658,281 | 8/1997 | Heard . |
| 5,667,526 | 9/1997 | Levin . |
| 5,674,220 * | 10/1997 | Fox et al. ................................. 606/51 |
| 5,693,051 | 12/1997 | Schulze et al. . |
| 5,700,261 | 12/1997 | Brinkerhoff . |
| 5,702,390 * | 12/1997 | Austin et al. ........................ 606/41 |
| 5,766,166 | 6/1998 | Hooven . |
| 5,769,849 | 6/1998 | Eggers . |
| 5,776,128 | 7/1998 | Eggers . |
| 5,776,130 | 7/1998 | Buysse et al. . |
| 5,827,281 | 10/1998 | Levin . |
| 5,951,549 | 9/1999 | Richardson et al. . |

* cited by examiner

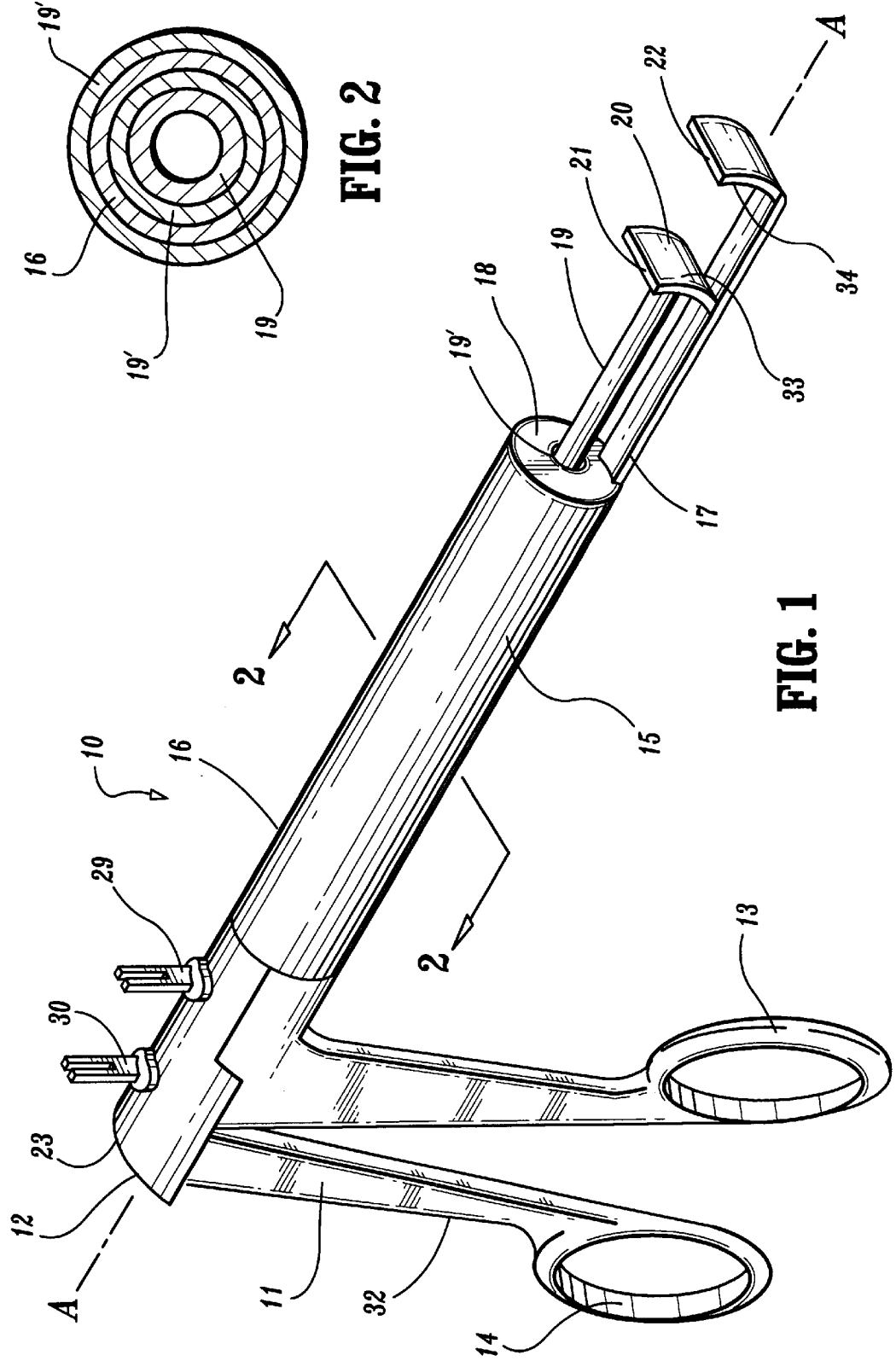

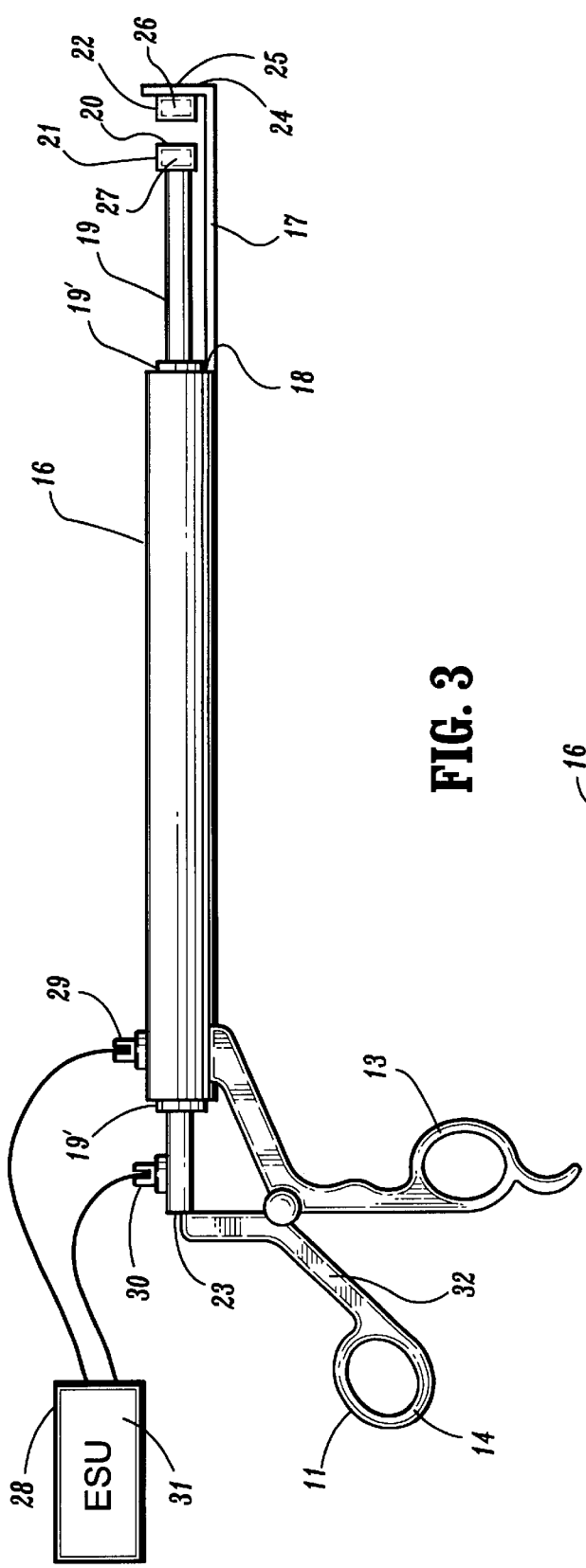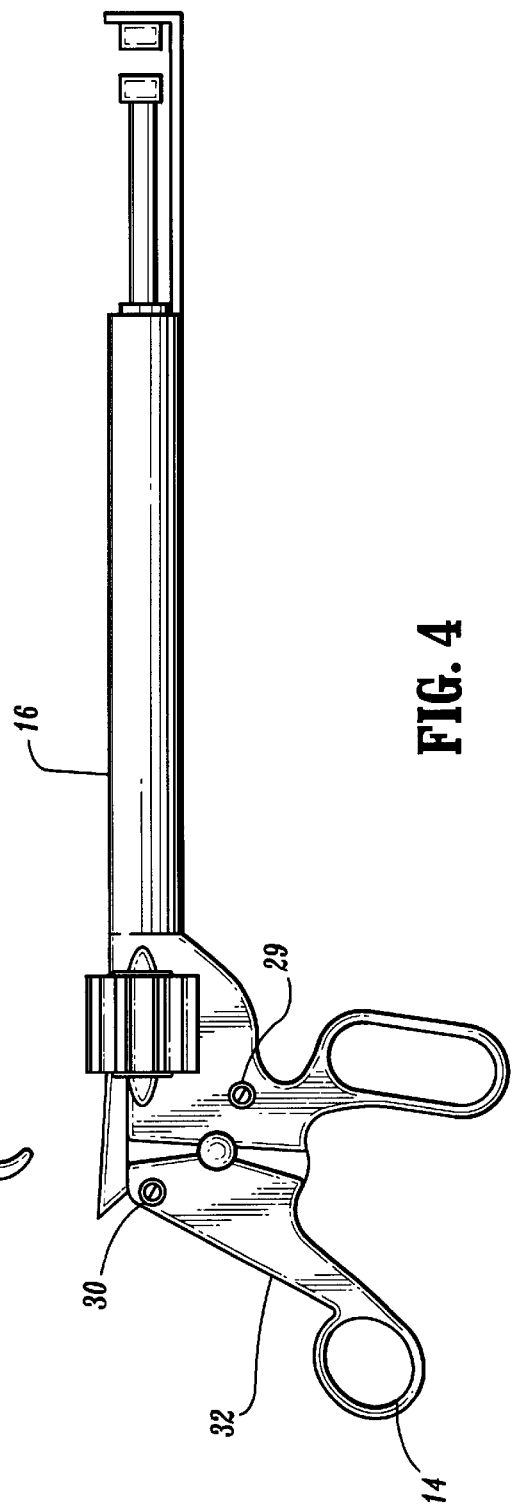
FIG. 3
FIG. 4

APPARATUS AND METHOD FOR SEALING AND CUTTING TISSUE

FIELD OF THE INVENTION

This relates to an apparatus and method for cutting and sealing blood vessels or tissue using a bipolar linear travel device that compresses the tissue or vessel and then RF power is applied to seal the tissue and cut the tissue.

BACKGROUND OF THE DISCLOSURE

In order to seal blood vessels during surgery, for the purpose of defunctionalizing the vessels or to halt or prevent bleeding, radiofrequency (RF) energy can be applied to the vessel structure instead of staples or clips. Traditionally, forceps are used to create a single seal per application with bipolar RF energy. Normally, forceps that have a hinge between the tines that press against either side of the vessel are clamped about tissue and power is applied. Problems are sometimes encountered with this technique because of the forceps bending or the lack of parallelism between the tines thus affecting how the tissue or vessel is compressed and sealed.

U.S. Pat. No. 5,585,896 has a percutaneous device for sealing openings in blood vessels. A balloon is inserted into the vessel and then inflated to force the vessel wall into a fixation collar.

U.S. Pat. No. 5,383,897 has a device for sealing punctures in blood vessels by conforming to the inner lumen of the vessel and placing barbs in the vessel for the purpose of sealing.

U.S. Pat. No. 5,391,183 has a device for sealing punctures in vessels by inserting hemostatic material into the puncture site and around the outside of the vessel, for the purpose of closing the puncture site.

U.S. Pat. No. 5,437,292 has a percutaneous device to seal arterial or venous puncture sites, whether accidental or intentional, which mixes fibrinogen and thrombin to form a gel around the puncture site to provide occlusion.

U.S. Pat. No. 5,411,520 has a device for percutaneously sealing blood vessels that slides down a holding catheter and enters the blood vessel with an anchor and collagen plug.

U.S. Pat. No. 5,415,657 has a device that approaches the puncture in the blood vessel, engages the outer surface and applies energy to provide hemostasis.

U.S. Pat. No. 5,429,616 has a device for sealing punctures in vessels by applying a fluid and then compressing the edges while it seals.

U.S. Pat. No. 5,441,517 has a system for sealing punctures in blood vessels by mechanically inserting a plug with an anchor to seal the puncture.

U.S. Pat. No. 5,425,739 discloses a stent placed inside the vessel to seal it or placed in such a way as to anastomose the vessel edges.

U.S. Pat. No. 5,354,271 discloses a sliding sheath for closing puncture sites that has two parts that expand radially outward and may use an accordion shape if a catheter.

U.S. Pat. No. 5,342,393 is a device that repairs punctures in vessels by clamping the tissue from both inside and outside of the vessel. Riveting is used to close the clamped sections and heat may be applied to separate the rivet from the delivery system. This device does apply heat energy but only to separate the rivet from the closure site.

U.S. Pat. No. 5,176,695 is a monopolar laparoscopic mechanical cutting device with a linear reciprocating blade that sharply cuts tissue residing in its slot. The present bipolar invention does not contain a sharp blade since it seals and cuts using RF energy.

U.S. Pat. No. 3,862,630 is a device wherein ultrasonic energy is used to close off blood vessels by mechanical vibration and frictional rubbing. Any heating of the tissue is a minimal and superficial byproduct of the mechanical vibration used to seal vessels.

U.S. Pat. No. 2,011,169 is a surgical electrode with end jaws that are U-shaped and nest one inside the other. They are not insulated from each other and thus are monopolar. In the present invention the jaws are insulated and bipolar. The jaws of '169 are mounted on an endoscope. They do not fit together as in the present invention and are designed more for the purpose of removing bites out of tissue and coagulating at the same time.

All of the above devices are different from the disclosure herein for several reasons. These devices are made for wound puncture closure. This implies that a viable flow channel will remain within the lumen of the blood vessel after each device is applied. The device now disclosed remains external to the blood vessel where no puncture site would normally exist either before or after the procedure. The present device and method seals the blood vessel, and thus does not provide a pathway for blood as do the prior devices discussed. In most cases, after the sealing with the instant device and method, the vessel will still be intact, although with a seal across it. In addition, the mere clamping by the disclosed device does not seal the blood vessel. It is the application of RF energy that forms an autologous clamp causing a fusion of the intima to provide the seal.

Therefore to solve the difficulties of the prior devices a patient contacting instrument for holding and applying electrosurgical energy is shown and described. During surgical dissection, blood vessels are frequently encountered that need to be sealed and thus defunctionalized. To do this in a safe, reliable manner so the vessel is properly sealed and will not leak, a tool that applies energy to create an autologous clip is valuable and required. The device and method are briefly described. A long tube connects to one side of a bipolar power supply. The tube moves longitudinally, that is along its long axis to meet against and compress the vessel with an endpiece. The two pieces that meet on either side of the vessel could be flat, curved, triangular, angled, notched, or other shapes, as long as one fits the other. If the endpieces are of some shape other than flat, this increases the surface area that traverses the vessel creating a longer seal in the vessel without increasing the diameter of the end pieces. An applied pulse of RF power cuts the tissue after sealing. The device and method when tested on fresh vessels produced a burst pressure adequate to prove a solid seal.

Advantages of the current device and method are the parallel axial closure of the end pieces to provide a compact bipolar sealer and prevent shorting. An in-line force transducer could provide feedback information on the applied force used during surgery. The device is bipolar to assure added safety by confinement of RF current flow through the tissue between the bipolar electrodes at the end of the device.

SUMMARY OF THE INVENTION

An axially elongate bipolar tissue sealer or cutter for application of electrosurgical energy by a surgeon to the tissue and bodily fluids of a patient preferably has a handle for holding and manipulation by the surgeon. A chassis carried on the handle may extend axially relative to the handle and away from the surgeon. The chassis may be moveable to and from the handle along the axis. The chassis may have a handle end and a distal end. A tube could be carried for axial movement relative to or along the chassis. The tube is elongate relative to the chassis and has a surgeon end and a patient end disposed along its axis in the preferred embodiment.

An effector on the patient end most preferably is in position to first contact tissue upon movement axially away from the handle by the surgeon. The effector is preferably of a material for conducting electrosurgical energy. A member may be supported by the distal end of the chassis in position opposite the patient end of the tube. A part on the member at the distal end thereof is most preferably transversely located relative to the tube axis. The part may be made of a material for conducting electrosurgical energy and to act as an opposed end effector.

A first bipolar electrosurgical electrode can be electrically connected to the effector of the patient end. A second bipolar electrosurgical electrode could be electrically connected to the part or opposed end effector. The second bipolar electrosurgical electrode is electrically isolated from the first bipolar electrosurgical electrode. An electrosurgical generator may be electrically coupled to the first and second electrosurgical electrodes. The electrosurgical generator can be arranged for selectively supplying bipolar electrosurgical energy across the first and second bipolar electrosurgical electrodes.

A mechanical activator is most preferably movably supported on the handle for use by the surgeon. The activator most preferably connects to the tube for axially moving the patient end and its end effector thereof toward or away from the part or opposed end effector. The tissue and bodily fluid between the end effectors may be sealed or cut by application of axial compression and bipolar electrosurgical energy between the first and second electrosurgical electrodes.

The end effector and the part or opposed end effector preferably include partial mating complimentary sealing or cutting surfaces for partial mating engagement upon axial movement along the axis toward one another. The end effector and/or port can be removably attached to patient end and/or member. The complimentary surfaces may be partially mated and curvelinear for providing more tissue contacting area than flat surfaces would. Alternatively, the partial mating complimentary surfaces might be parallel but skewed to the axis to provide elongate contact with axial movement between the end effector and the port. The partial mating complimentary surfaces could be substantially flat. The partial mating complimentary surfaces may be circular. The partial mating complimentary surfaces might be elliptical. The partial mating complimentary surfaces could also be triangular. The partial mating complimentary surfaces may include at least one conjugating rib and slot. The partial mating complimentary surfaces could include one or more ribs and mating slots.

A method of using an elongate along an axis tissue sealer or cutter for application by a surgeon of bipolar electrosurgical energy to tissue and bodily fluids of a patient may seal or cut. The method may have the steps of holding and manipulating by a surgeon of a handle. Extending axially a chassis and/or a tube carried on the handle might be a step. The method can have the step of moving along the axis the chassis and/or the tube with the handle. Carrying the tube for axial movement relative to and along the chassis might be a step of the method. The method step may include positioning an effector on a patient end of the tube for first contact with tissue upon movement axially away from the handle by the surgeon. Using a supported member on a distal end of the chassis in position away from the patient end of the tube can be a step of the method. The method may have the step of having a part located transversely relative to the axis and on the member.

The method of using may be performed with a first bipolar electrosurgical electrode coupled to the end effector of the patient end and a second bipolar electrosurgical electrode coupled to the part. Electrically isolating the second bipolar electrosurgical electrode from the first bipolar electrosurgical electrode is another preferred step of the method of using. The method preferably has the step of selectively electrically coupling an electrosurgical generator to the first and second electrosurgical electrodes to supply bipolar electrosurgical RF energy from the electrosurgical generator to the first and second bipolar electrosurgical electrodes. The method most preferably has the step of a surgeon using a mechanical activator that is movably supported on the handle. Moving axially with the activator the patient end and/or the opposed end effector so that tissue and bodily fluid therebetween may be sealed or cut between the end effector and the part through the application of compression and bipolar electrosurgical energy between the first and second electrosurgical electrodes is a preferred step.

The method may have the steps of applying the provided effector with the partially mating complimentary sealing or cutting surfaces, and partially mating engagement of the complimentary sealing or cutting surfaces upon axial movement toward one another along the axis. The method might use the step of removably attaching the part and/or end effector to the member and the chassis respectively. The method has the step of using partially mating the complimentary surfaces engagable along curvelinear paths for providing more tissue contacting area than between flat surfaces. The method has the step of using the partially mating the complimentary surfaces preferably parallel but along a plane skewed to the axis to provide elongate contact with axial movement between the end effector and the port.

The method may have the step of using the partially mating complimentary flat surfaces that are perhaps along the planes of the flat surfaces. The method could have the step of using partially mating complimentary circular surfaces that might be along the arcs of the circular surfaces. The method might have the step of using partially mating complimentary elliptical surfaces which are preferably along the curves of ellipses. The method can have the step of using partially mating complimentary triangular surfaces along edges of the triangles. The method could have the step of using partially mating complimentary surfaces by engaging at least one conjugating rib with a slot. The method may have the step of using partially mating complimentary surfaces that may include one or more ribs and companion slots.

BRIEF DESCRIPTION OF THE DRAWINGS

FIG. 1 is a perspective view of an elongated tubular bipolar tissue sealer or cutter for application by a surgeon of electrosurgical energy to the tissue, the sealer or cutter slides along its axis with an internal, concentric sliding portion for axially bring together the end effectors.

FIG. 2 is a view in cross section as would be seen along lines 2—2 in FIG. 1.

FIG. 3 is a side view of a reusable elongate tubular bipolar tissue sealer or cutter as in FIG. 1 with one of the various end effectors having partially mating complimentary surfaces.

FIG. 4 is a side view of a disposable elongate tubular bipolar tissue sealer or cutter as in FIG. 1 with one of the various end effectors having partially mating complimentary surfaces.

DETAILED DESCRIPTION OF THE INVENTION

Figure 5:
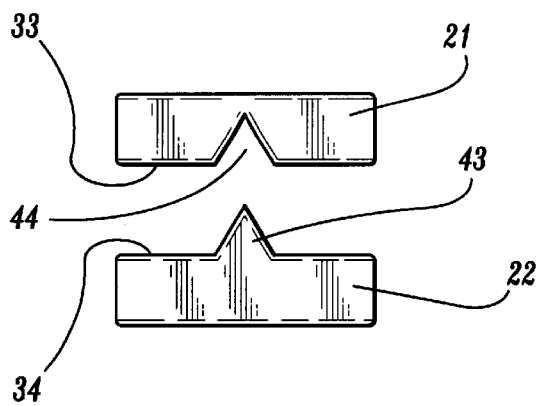
FIG. 5 is an enlarged top view of the part and of the end effector with partially mating complimentary surfaces that nest with V shaped conjugating jaws.

FIG. 1 is a perspective view of an elongate tubular bipolar tissue sealer or cutter 10 for application by a surgeon of electrosurgical energy to tissue. A handle 11, for holding and manipulation by the surgeon, is on a proximal end 12 of the elongate bipolar tissue sealer or cutter 10. The handle 11 has both first and second handle grips 13 and 14, respectively. A chassis 15, carried on the handle 11 by mechanical connection with the first handle grip 13, extends axially along axis "A" relative to the handle 11 and away from the surgeon a distance adequate to reach the patient's operative site. The chassis 15 is comprised of at least two parts. The first is an outer tube 16 which extends from the handle 11 along the axis "A." The outer tube 16 is fixed on the chassis 15. The second part is a member or chassis extension 17 extending from a patient end 18 of the outer tube 16, also along the axis "A." An inner tube 19 is moveable to and from the handle 11 in the preferred embodiment. The inner tube 19 is guided along the axis "A." The inner tube 19 connects to the second handle grip 14 for surgeon access. A distal end 20 is on the inner tube 19 and faces the operative site. The elongate tubular sealer or cutter 10 thus in part slides along its axis "A" with inner tube 19 which is an internal, concentric slider to axially bring together end effectors 21 and 22. Inner tube 19 is telescopically carried, in the preferred embodiment, on the chassis 15 for axial movement relative to and therealong. The inner tube 19 moves relative to the chassis 15, a surgeon end 23 and the distal end 20 which are disposed along the axis "A" thereof as shown in FIGS. 1 and 3. FIG. 2 is a view of the inner and outer tubes 19 and 16 in cross section as would be seen along lines 2—2 in FIG. 1. The preferred outer and inner tubes 16 and 19 are metallic and thus should be insulated from each other and from the user by a coating 19' as seen in FIG. 2.

End effector 21 on the distal end 20 is in position to contact tissue upon movement axially away from the handle 11 by the surgeon's manipulation of second handle grip 14. FIG. 3 is a side view of the reusable elongate tubular structure of FIG. 1 with both of the various end effectors 21 and 22 shown from the side. The effector 21 and 22 are made of materials for conducting electrosurgical energy such as metal, conductive polymer or ceramic. The end effector 22 has member (jaw member) 24 supported by the chassis extension 17 normal thereto in position opposite the patient end 20 of the inner tube 19. A part 25 on the member 24 thereof is transversely located relative to the axis "A" in FIG. 1. The end effectors 21 and 22 are thus opposed for engagement upon relative axial displacement of the inner tube 19 and/or chassis 15. FIG. 4 is a side view of a disposable elongate tubular structure of FIG. 1 with one of the various end effectors 21 and 22 shown from the side in FIG. 3. As shown in FIG. 3 the chassis extension 17, member 24, and part 25 are made for conducting electrosurgical energy. Of course, insulation can be added as needed to direct the bipolar electrosurgery to the space between the end effectors 21 and 22.

A first bipolar electrosurgical electrode 26 for contact with the patient's tissue or bodily fluids is electrically coupled to the effector 22 beyond the patient end 18. A second bipolar electrosurgical electrode 27 is electrically coupled to the effectors 21 and 22 for contact with the patient's tissue or bodily fluids. The second bipolar electrosurgical electrode 27 is electrically isolated from the first bipolar electrosurgical electrode 26 but is in position to deliver bipolar electrosurgical energy across tissue held therebetween. An electrosurgical generator 28, in FIG. 3, is electrically coupled to the first and second electrosurgical electrodes 26 and 27 through terminals 29 and 30, respectively. The electrosurgical generator 28 can be arranged for selectively supplying bipolar electrosurgical energy to the first and second bipolar electrosurgical electrodes 26 and 27. Selective application of electrosurgical energy is in response to the surgeons control and/or a sensor 31 in the electrosurgical generator 28. Sensor 31 may measure impedance across the tissue between the electrodes 26 and 27.

A mechanical activator 32, in FIG. 3, is preferably movably supported on the handle 11 for use by the surgeon. The mechanical activator 32 connects to the inner tube 19 for axially moving the end effector 21 thereof toward or away from the end effector 22 in the preferred embodiment. The tissue and bodily fluid therebetween may be sealed or cut between the end effectors 21 and 22 through the combined application of compression and bipolar electrosurgical energy between the first and second electrosurgical electrodes 26 and 27.

Figure 8:
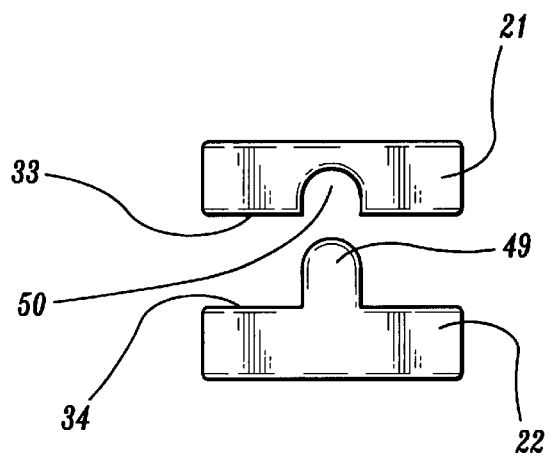
FIG. 8 is an enlarged top view of the part and the end effector with partially mating complimentary surface that nest with a pedistaled male and a flush female wherein both are U shaped conjugating jaws.
Figure 9:
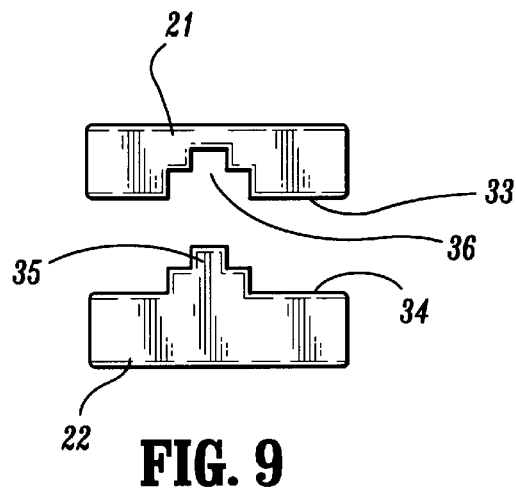
FIG. 9 is an enlarged top view of the part and end effector with partially mating complimentary surface that nest with a terraced male and a recessed female shaped to fit as conjugating jaws.
Figure 10:
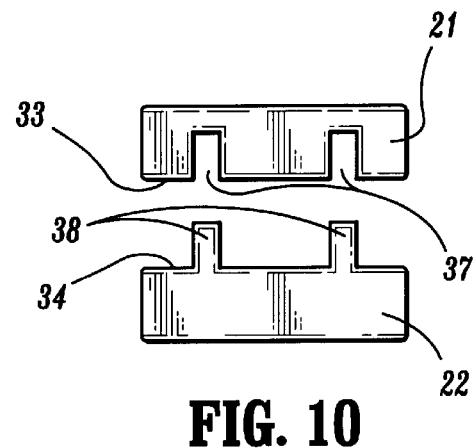
FIG. 10 is an enlarged top view of the part and the end effector with partially mating complimentary surfaces that nest with a pair of upstanding ribs and a conjugating pair of kerfs as the jaws.
Figure 11:
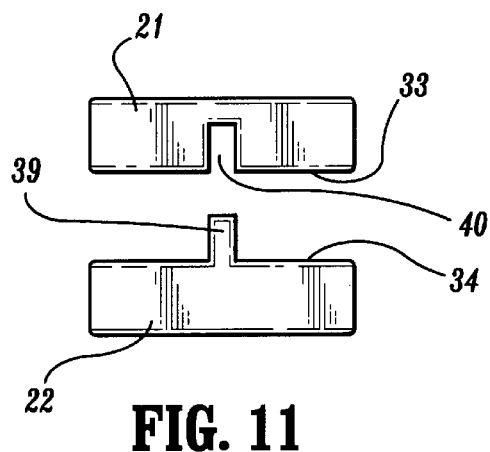
FIG. 11 is an enlarged top view of the part and the end effector with partially mating complimentary surfaces that nest with a single upstanding rib and conjugating kerf as the jaws.
Figure 12:
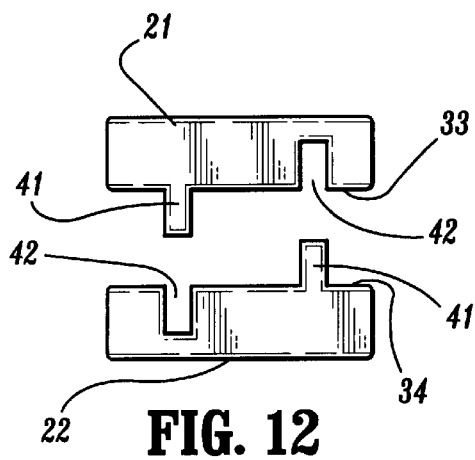
FIG. 12 is an enlarged top view of the part and the end effector with partially mating complimentary surfaces that nest with a pair of upstanding ribs and conjugating kerfs wherein therein one rib and one kerf is on the end effector across from its companion kerf and rib on the part as the jaws.
Figure 13:
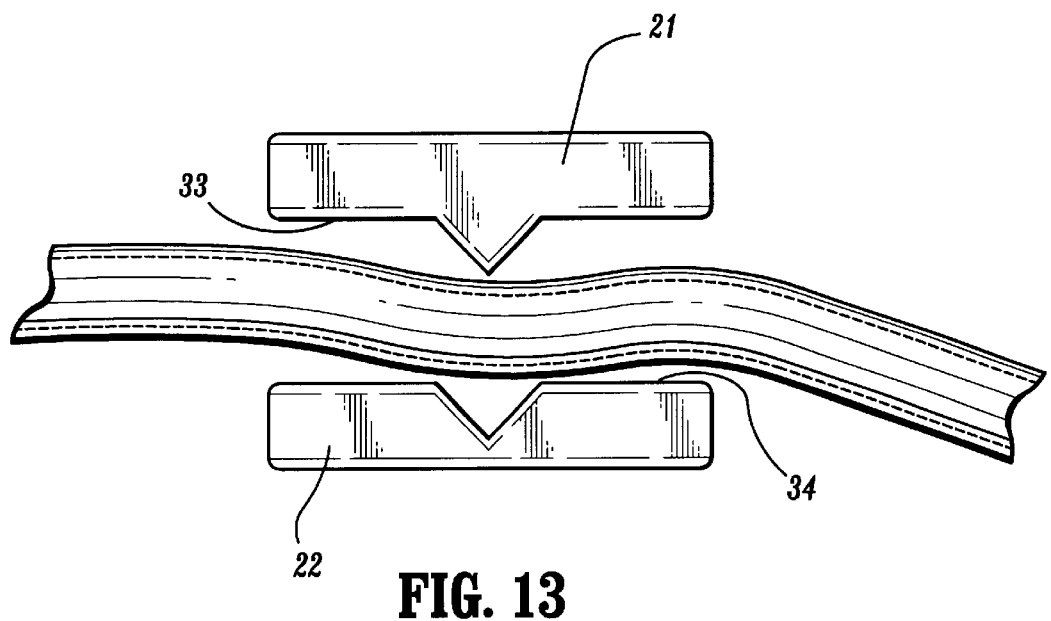
FIG. 13 illustrates the conjugating jaws of FIG. 5 with a vessel the between prior to sealing.
Figure 14:
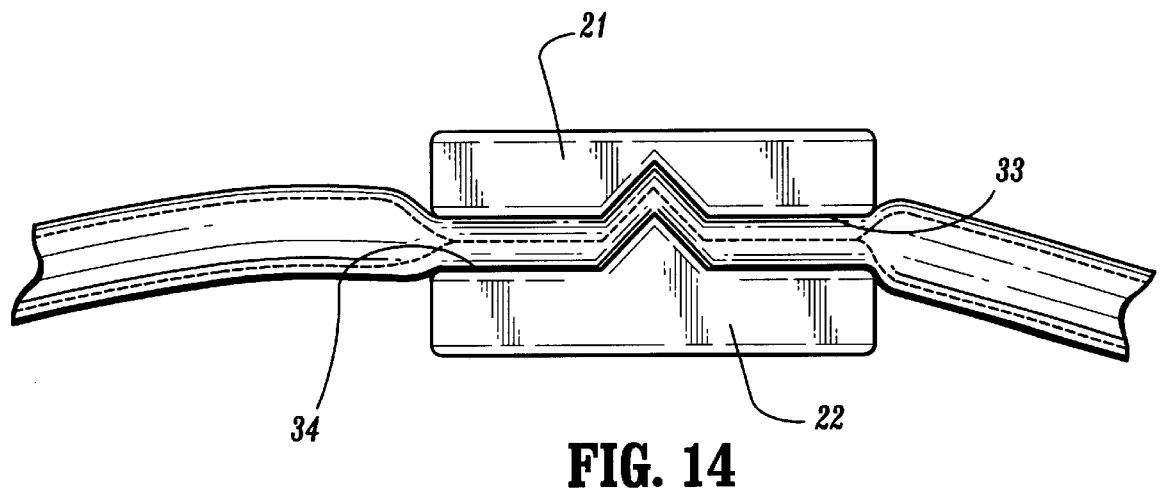
FIG. 14 illustrates the conjugated jaws of FIG. 5 with a vessel therebetween during sealing.
Figure 15:
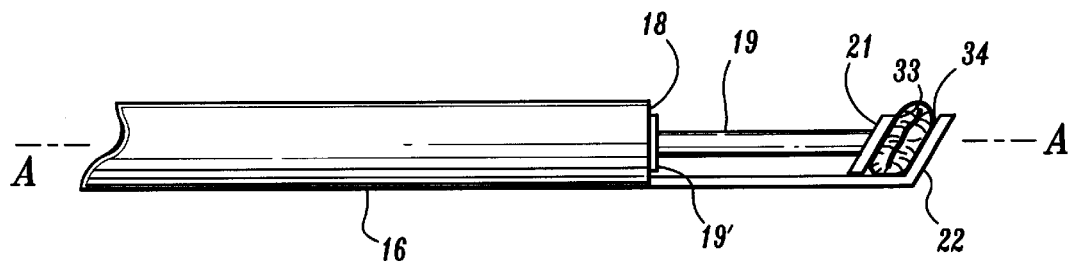
FIG. 15 is a partial enlarged view of the end effector and the part of FIG. 1 viewed from above with an open vessel clamped therebetween during the process of sealing.

The end effectors 21 and 22 include complimentary sealing or cutting surfaces 33 and 34 for partial mating engagement upon their axial movement toward one another along the axis "A." FIG. 13 illustrates end effectors 21 and 22 or the conjugating jaws of FIG. 5 with a vessel therebetween prior to sealing. Similarly, FIG. 14 illustrates end effectors 21 and 22 or the conjugating jaws of FIG. 5 with a vessel therebetween during sealing. The end effectors 21 and 22 could be removably attached to the member 24 and/or the inner tube 19, respectively. FIG. 15 is a partial enlarged view of the end effectors 21 and 22 of FIG. 1 viewed from the side with an open vessel clamped therebetween during the method or process of sealing. The partial mating complimentary surfaces 33 and 34 in FIG. 8 are curvelinear for providing more tissue contacting area than flat surfaces of the same width would. In FIG. 8 the end effectors 21 and 22 have conjugating complimentary surfaces 33 and 34 that nest configured with a pedistaled male part 49 and a mating U shaped female part 50 for the jaws. FIG. 9 is an enlarged top view of end effectors 21 and 22 showing conjugating surfaces that nest with a male part 35 terraced and a female part 36 shaped to fit as jaws. FIG. 10 is an enlarged top view of end effectors 21 and 22 showing conjugating surfaces that nest with a pair of upstanding ribs 38 and a complimentary pair of kerfs 37 as the jaws. FIG. 11 is an enlarged top view of the end effectors 21 and 22 showing conjugating surfaces that nest with a single upstanding rib 39 and a complimentary kerf 40 as the jaws. FIG. 12 is an enlarged top view of end effectors 21 and 22 showing conjugating surfaces that nest with a pair of upstanding opposite ribs 41 and complimentary opposed kerfs 42 wherein therein one rib 41 is on each of the end effectors 21 and 22 across from its complimentary kerf 42 on the opposite end effectors either 21 or 22.

Figure 6:
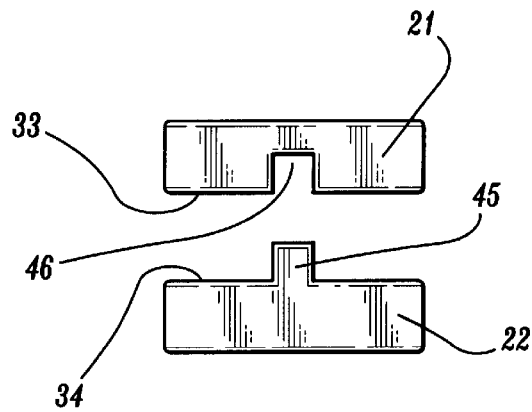
FIG. 6 is an enlarged top view of the part and the end effector with partially mating complimentary sure that nest with rib and slot conjugating jaws.
Figure 7:
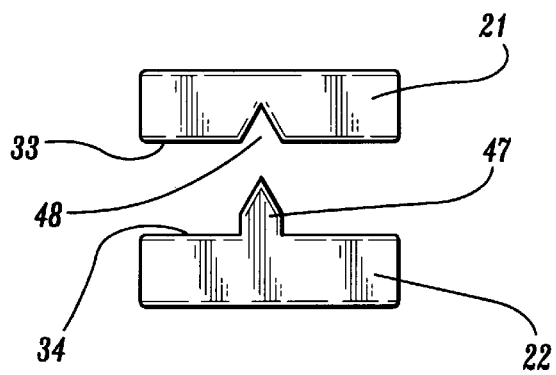
FIG. 7 is an enlarged top view of the part and the end effector with partially mating complimentary surfaces that nest with a pedistaled male and a flush female wherein both are V shaped conjugating jaws.

Any complimentary mating curvelinear jaws even "S" shaped or those shown in FIG. 1 could be arranged to provide more surface area for contact than the flat surfaces defined by the cords thereacross. FIG. 5 is an enlarged top view end effectors 21 and 22 showing conjugating surfaces 33 and 34 that nest with V shaped complimentary jaws 43 and 44. FIG. 6 is an enlarged top view of end effectors 21 and 22 showing conjugating surfaces 33 and 34 that nest with a rib 45 and a channel 46 as complimentary jaws. FIG. 7 is an enlarged top view of end effectors 22 and 23 showing conjugating surfaces 33 and 34 that nest with a male part pedistaled 47 and V shaped female part 48 as complimentary jaws.

The partial mating complimentary surfaces 33 and 34 might be parallel but skewed to axis "A" as in FIG. 15 to provide elongate contact with axial movement between the inner tube 19 and chassis 15 thus keeping the size of the laparoscopic portal through which the end effectors 21 and 22 must pass to a minimum transverse dimension. The partial mating complimentary surfaces 33 and 34 could be substantially flat as in FIGS. 3 and 4. The partial mating complimentary surfaces 33 and 34 may be circular sections such as appear in FIGS. 1 and 8. The partial mating complimentary surfaces 33 and 34 might be elliptical and thus similar to FIGS. 1 and 8 with the curvatures being a part of an ellipse instead of a circle. Because of the perspective showing in FIG. 1, the observable differences in such an illustration between a circle and an ellipse can not be perceived. The partial mating complimentary surfaces 33 and 34 could also be triangular as in FIGS. 5, 7, 13 and 14. The partial mating complimentary surfaces 33 and 34 may include at least one conjugating rib and slot as in FIGS. 6 and 11. The partial mating complimentary surfaces 33 and 34 could include several ribs as in FIGS. 10 and 12.

A method of applying the elongate tubular bipolar tissue sealer or cutter 10 along an axis "A" includes use by a surgeon to deliver bipolar electrosurgical energy to the tissue and bodily fluids of a patient. The method has the steps of holding and manipulating the handle 11 by the surgeon. Extending axially inner tube 19 and/or the chassis 15 carried on the handle 11 away from the surgeon is a step. The method can have the step moving the inner tube 19 relative to the chassis 15 along the axis "A." Carrying inner tube 19 for axial movement relative to and along the chassis 15 is a step of the preferred method. The method step includes positioning end effector 22 on the patient end 18 to first contact tissue upon movement axially of the inner tube 19 by the surgeon. Using a supported member 24 the chassis 15 is a step of the method. The method may have the step of using a part 25 located transversely relative to the axis "A" and on the member 24.

The method of using has a first bipolar electrosurgical electrode 26 coupled to the end effector 22 extending from the patient end 18 and a second bipolar electrosurgical electrode 27 coupled to the end effector 21. Electrically isolating the second bipolar electrosurgical electrode 27 from the first bipolar electrosurgical electrode 26 is another preferred method step for using. The method preferably has the step of selectively coupling electrically an electrosurgical generator 28 to the first and second electrosurgical electrodes to supply bipolar electrosurgical energy from the electrosurgical generator to the first and second bipolar electrosurgical electrodes 26 and 27. The method most preferably has the step of a surgeon using a mechanical activator 32 movably supported on the handle 11. Moving axially with the mechanical activator 32 the inner tube 19 and the end effector 21 thereof toward or away from the end effector 22 so that tissue and bodily fluid therebetween may be sealed or cut between the end effectors 21 and 22 the application of compression and bipolar electrosurgical energy between the first and second electrosurgical electrodes 26 and 27 is a preferred step.

Figure 16:
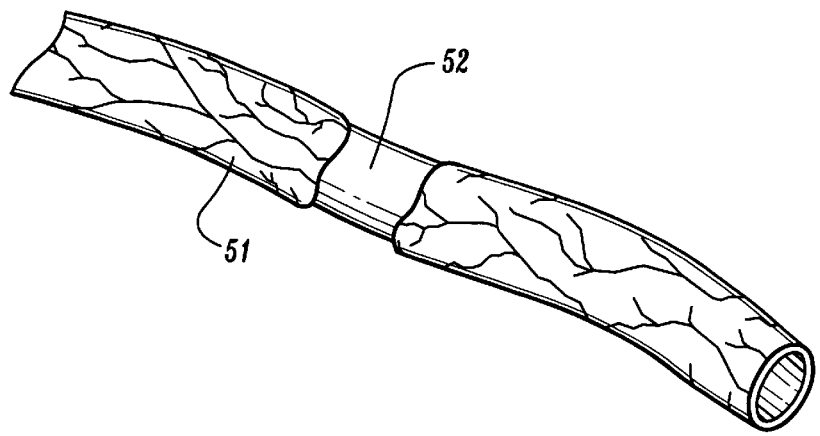
FIG. 16 is a perspective illustration of a sealed vessel.

The method may have the steps of applying the provided end effectors with partially complimentary sealing or cutting surfaces 33 and 34, and partially mating engagement of the complimentary sealing or cutting surfaces 33 and 34 upon axial movement toward one another along the axis "A." FIG. 16 is a perspective illustration of a sealed vessel 51 as a consequence of performing the method to form seal 52. The method might use the step of choosing to removably attach the end effectors 26 and 27, inner tube 19 and the chassis 15, respectively. The method has the step of using partially mating the complimentary surfaces 33 and 34 engagable along curvelinear paths for providing more tissue contacting area than between flat surfaces. The method has the step of using the partially mating the complimentary surfaces 33 and 34 preferably parallel along a plane skewed to the axis "A" to provide elongate contact with axial movement between the inner tube 19 and chassis 15.

The method has the step of using the partially mating complimentary flat surfaces 33 and 34 that are perhaps along the planes of the flat surfaces. The method has the step of using the partially mating complimentary circular surfaces 33 and 34 that might be along the arcs of the circular surfaces. The method has the step of using the partially mating complimentary elliptical surfaces 33 and 34 which are preferably along the curves of the ellipses. The method has the step of using the partially mating complimentary triangular surfaces 33 and 34 that can be along edges of the triangles. The method has the step of using the partially mating complimentary surfaces 33 and 34 by engaging at least one conjugating rib and slot. The method has the step of using the partially mating complimentary surfaces 33 and 34 that include one or more ribs.

Figure 17:
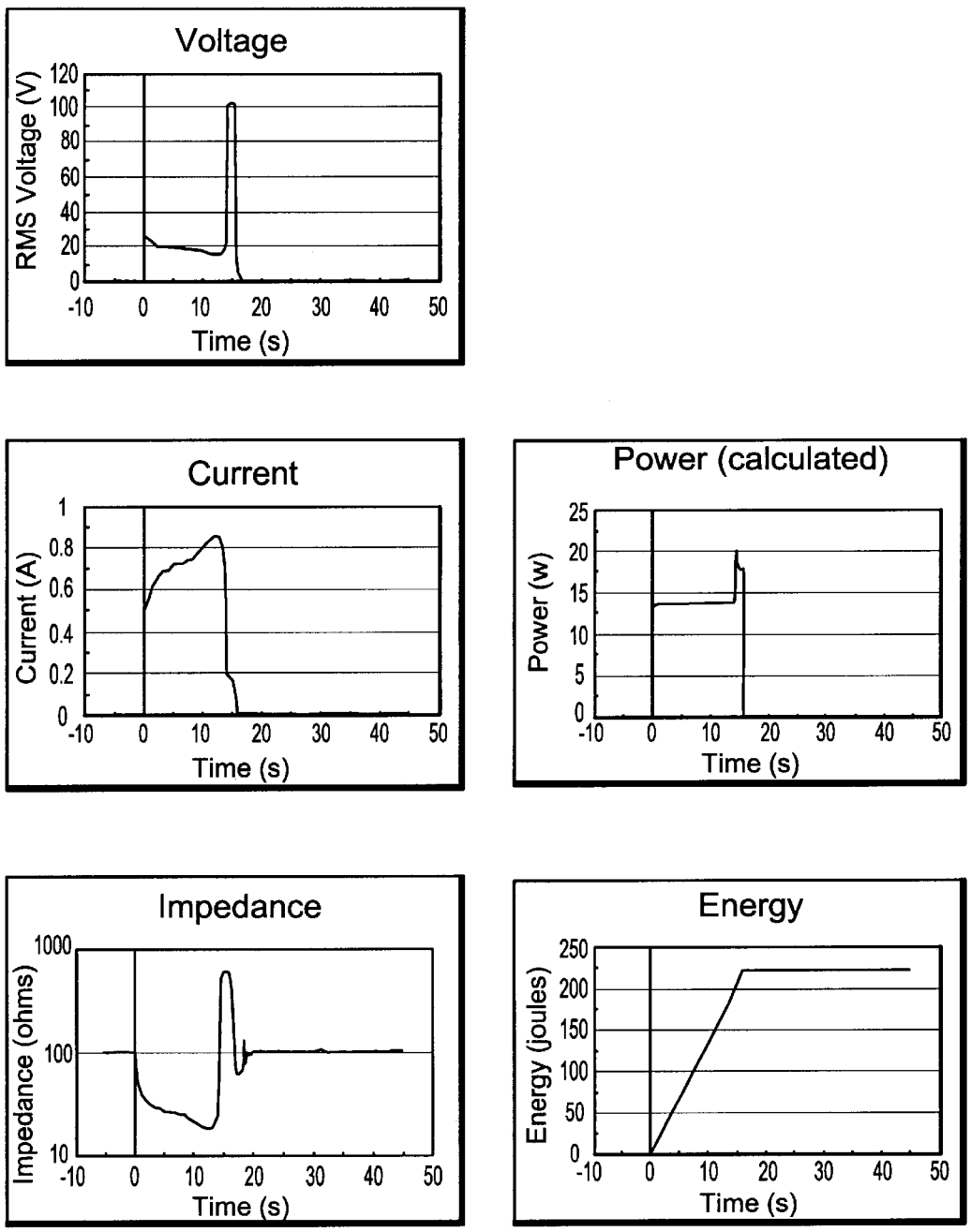
FIG. 17 shows voltage, current, impedance, power, and energy captured during sealing of a splenic artery.

As a result of laboratory testing of a model of the bipolar tissue sealer or cutter results have shown excellent performance in sealing a range of vessels of various sizes. The bipolar tissue sealer or cutter with linear travel was tested on freshly excised porcine splenic arteries ranging from 1.8 to 3.3 mm. A single activation of power (14 W, 500 kHz) was used on each vessel firmly clamped between the end effector bipolar electrodes. FIG. 17 shows the voltage, current, impedance, power, and energy during activation on a 2.6 mm porcine splenic artery with the bipolar device shown in FIG. 15. The voltage ranges from 18–23 volts until the impedance rises at about 14 sec. At this point, the vessel is sealed and the power is manually switched off The impedance curve shows an initial decrease as the vessel is heated with radiofrequency energy, down to about 20 ohms. The rapid increase to about 200 ohms signals that the vessel is desiccated and sealing process is over.

Data, shown in the graphs of FIG. 17, display the voltage, current, impedance, power and energy during the activation of 17 sec. achieved with an elongated tubular bipolar tissue sealer or cutter as shown in FIG. 15. Activation times ranged from 12–28 sec. Energy applied ranged from 170–400 joules. Contact impedance ranged from 20–80 ohms, depending on vessel size and shape of end effectors. If the end effectors of FIG. 5 were used, the contact impedance would decrease due to the larger contact area with the vessel. Vessel size affects impedance as well.

The vessels were closely examined after each sealing and found to have no charring. In 2 out of 13 trials, the vessel was adherent to one of the end effectors. Histological analysis showed that the vessel walls were completely welded with the integrity of the intima, adventitia, and media completely lost. The proteins were melted and a semi-translucent weld resulted. Adjacent to the weld site, the vessel wall was relatively normal.

The preferred elongate tubular bipolar tissue sealer or cutter 10 for application of electrosurgical energy to tissue by a surgeon as covered in the claims that follow has structure that slides along its axis "A" with an internal, concentric sliding portion. The inner or inside sliding tube 19 is attached to the proximal end effector 21 and the external fixed tube or chassis 15 connects to the distal end effector 22 in the preferred embodiment. The two end effectors 21 and 22 are matched so that the distal end effector 22 fits snugly against the proximal end effector 21. These end effectors 21 and 22 can be any of a number of conjugating shaped pairs including triangular, spherical, rectangular, with or without a notch. The notch is not just for alignment but also may define a sharp edge to sever the tissue or vessel by application of a pulse of high-power RF to the clamped site of tissue in between the end effectors 21 and 22. In the preferred embodiment, the handle 11 is squeezed so the inner tube 19 slides away the user and the chassis 15 is fix in relation to the inner tube 19 as the end effectors 21 and 22 act on the tissue therebetween. Of course it can be reversed so the chassis 15 moves and the inner tube 19 is fixed.

What is claimed is:

1. An elongate bipolar tissue sealer for application by a surgeon of electrosurgical energy to the tissue and bodily fluids of a patient, the sealer comprising:

a handle for holding and manipulation by the surgeon;

a chassis carried on the handle extending distally relative to the handle, the chassis having a handle end and a distal end disposed along the axis;

a tube carried for axial movement relative to and along the chassis and the handle, the tube elongate relative to the chassis, the tube having a surgeon end and a patient end disposed along the axis thereof;

an effector on the patient end in position to first contact tissue upon movement of the tube relative to the chassis and axially away from the handle by the surgeon, the effector of a material for conducting electrosurgical energy;

a member supported by the distal end of the chassis extending past the patient end of the tube;

a part on the member at the distal end thereof, the part transversely located relative to the axis in position opposite the patient end, the part of a material for conducting electrosurgical energy;

a first bipolar electrosurgical electrode electrically connected to the effector of the patient end;

a second bipolar electrosurgical electrode electrically connected to the part, the second bipolar electrosurgical electrode electrically isolated from the first bipolar electrosurgical electrode;

an electrosurgical generator electrically coupled to the first and second electrosurgical electrodes, the electrosurgical generator for selectively supplying bipolar electrosurgical energy to the first and second bipolar electrosurgical electrodes;

a mechanical activator movably supported on the handle for use by the surgeon, the activator connected to the tube, the activator for axially moving the patient end and the effector thereof toward from the part so that tissue and bodily fluid therebetween may be sealed between the effector and the part through the application of compression and bipolar electrosurgical energy between the first and second electrosurgical electrodes.

2. The bipolar tissue sealer of claim 1 wherein the mechanical activator is connected to the chassis for relative movement of the tube and chassis.

3. The bipolar tissue sealer of claim 1 wherein the effector and the part include complimentary sealing surfaces which partially matingly engage upon axial movement toward one another along the axis.

4. The bipolar tissue sealer of claim 1 wherein the part and the effector are removably attached to one of the member and the chassis.

5. The bipolar tissue sealer of claim 3 wherein the surfaces are curvelinear for providing increased tissue contacting area.

6. The bipolar tissue sealer of claim 3 wherein the surfaces are parallel but skewed to the axis to provide elongate contact with axial movement between the member and chassis.

7. The bipolar tissue sealer of claim 6 wherein the surfaces are substantially flat.

8. The bipolar tissue sealer of claim 6 wherein the surfaces are circular.

9. The bipolar tissue sealer of claim 3 wherein the surfaces are elliptical.

10. The bipolar tissue sealer of claim 3 wherein the surfaces are triangular for meeting along edges thereof.

11. The bipolar tissue sealer of claim 3 wherein the surfaces include at least one conjugating rib and companion slot.

12. The bipolar tissue sealer of claim 3 wherein the surfaces include one or more ribs.

13. A method of using an elongate bipolar tissue sealer for application by a surgeon of electrosurgical energy to the tissue and bodily fluids of a patient, the method of sealing comprising:

holding and manipulating a handle;

a tube extending axially along an axis and carried on a chassis supported by the handle;

moving the tube relative to the handle along the axis, the chassis having a handle end and a distal end;

carrying the tube telescopically with the chassis for axial movement relative thereto and along the axis, the tube elongate relative to the chassis, the tube having a surgeon end and a patient end disposed along the axis thereof;

contacting tissue upon movement axially of an effector on the patient end with movement away from the handle and controlled by the surgeon, the chassis having a member extending from the distal end having a part in position opposite the patient end of the tube and transverse relative to the axis and on the member;

providing a first bipolar electrosurgical electrode coupled to the effector of the patient end and a second bipolar electrosurgical electrode coupled to the part;

electrically isolating the first bipolar electrosurgical electrode from the second bipolar electrode;

coupling electrically to an electrosurgical generator, the first and second bipolar electrosurgical electrodes;

providing movement of the patient end and the effector relative to the part thus sealing tissue and bodily fluid therebetween the effector and the part through the application of compression and bipolar electrosurgical energy between the first and second electrosurgical electrodes during use by the surgeon of a mechanical activator connected for relative movement of the tube or chassis.

14. The method of claim 13 wherein the first and second electrosurgical electrodes include complimentary sealing surfaces and the method further comprises the step of mating and engaging the complimentary sealing surfaces about tissue upon axially moving the first and second electrodes toward one another along the axis.

15. The method of claim 13 further comprising the step of removably attaching the part and the effector to the member and the chassis respectively.

16. The method of claim 14 further comprising the step of partially mating the complimentary surfaces which extend along curvelinear paths for providing increased contacting area.

17. The method of claim 14 further comprising the step of partially mating the complimentary surfaces which extend along planes skewed to the axis to provide elongate contact with relative axial movement between the tube and chassis.

18. The method of claim 14 further comprising the step of partially mating complimentary flat surfaces which extend along the planes of the flat surfaces that are perpendicular to the axis.

19. The method of claim 14 further comprising the step of partially mating complimentary circular surfaces having conjugating arcs.

20. The method of claim 14 further comprising the step of partially mating complimentary elliptical surfaces having conjugating curves.

21. The method of claim 14 further comprising the step of partially mating complimentary triangular surfaces having conjugating edges.

22. The method of claim 14 further comprising the step of partially mating complimentary surfaces by engaging at least one conjugating rib with a companion slot.

23. The method of claim 14 further comprising the step of partially mating complimentary surfaces including one or more ribs and associated slots.

* * * * *